(12) United States Patent
Ruediger et al.

(10) Patent No.: US 7,424,980 B2
(45) Date of Patent: Sep. 16, 2008

(54) NANO-ELECTROSPRAY NEBULIZER

(75) Inventors: Waldemar Ruediger, New Hope, PA (US); Richard Erich Gedamke, Highland Park, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 580 days.

(21) Appl. No.: 11/100,133

(22) Filed: Apr. 6, 2005

(65) Prior Publication Data

US 2005/0230498 A1 Oct. 20, 2005

Related U.S. Application Data

(60) Provisional application No. 60/560,462, filed on Apr. 8, 2004.

(51) Int. Cl.
- B05B 1/34 (2006.01)
- B05B 1/28 (2006.01)
- B05B 7/06 (2006.01)
- B01D 59/44 (2006.01)
- H01J 49/00 (2006.01)

(52) U.S. Cl. ............ 239/338; 239/294; 239/423; 239/424; 250/288

(58) Field of Classification Search ............ 239/338, 239/294, 423, 424, 86, 290, 337, 418, 424.5; 250/288

See application file for complete search history.

(56) References Cited

U.S. PATENT DOCUMENTS

| | | | |
|---|---|---|---|
| 4,125,225 A * | 11/1978 | Venghiattis | 239/338 |
| 5,122,670 A | 6/1992 | Mylchreest et al. | |
| 5,162,650 A | 11/1992 | Bier | |
| 5,170,053 A | 12/1992 | Hail et al. | |
| 5,171,990 A | 12/1992 | Mylchreest et al. | |
| 5,393,975 A | 2/1995 | Hail et al. | |
| 5,756,994 A | 5/1998 | Bajic | |
| 6,126,086 A * | 10/2000 | Browner et al. | 239/102.1 |
| 6,147,347 A * | 11/2000 | Hirabayashi et al. | 250/288 |
| 6,222,185 B1 | 4/2001 | Speakman et al. | |
| 6,410,915 B1 | 6/2002 | Bateman et al. | |
| 6,446,883 B1 * | 9/2002 | Huang et al. | 239/424.5 |
| 6,667,474 B1 * | 12/2003 | Abramson et al. | 250/288 |
| 2002/0190203 A1 | 12/2002 | Valaskovic et al. | |

FOREIGN PATENT DOCUMENTS

EP 1 308 708 5/2003

* cited by examiner

*Primary Examiner*—Darren W Gorman
(74) *Attorney, Agent, or Firm*—Terence J. Bogie

(57) ABSTRACT

A nebulizer is provided for use as an ion source for a mass spectrometer. The nebulizer facilitates alignment with a mass spectrometer target, reduces sample and nebulizer gas leakage, is easy to assemble and disassemble, and operates over a wide range of sample flow rates.

38 Claims, 7 Drawing Sheets

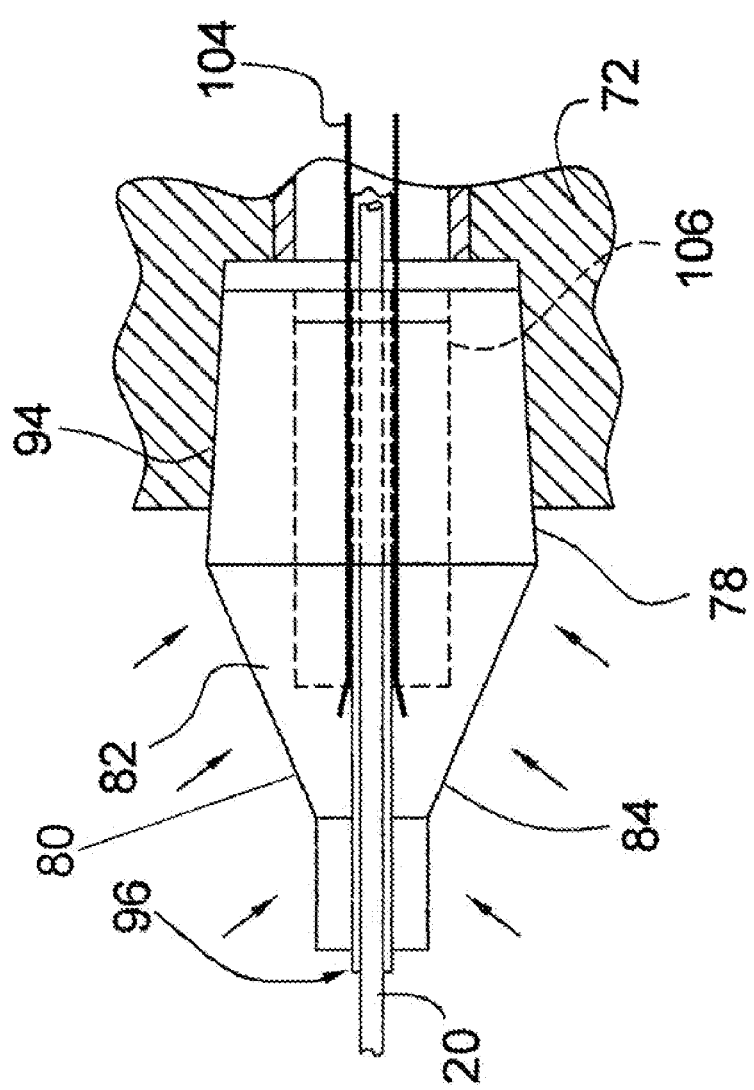
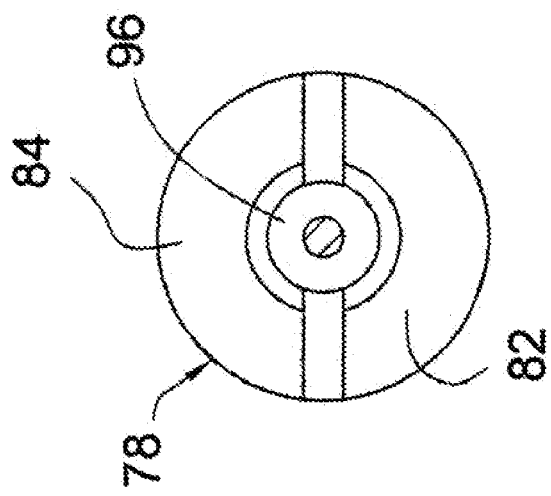
FIG. 4
FIG. 5

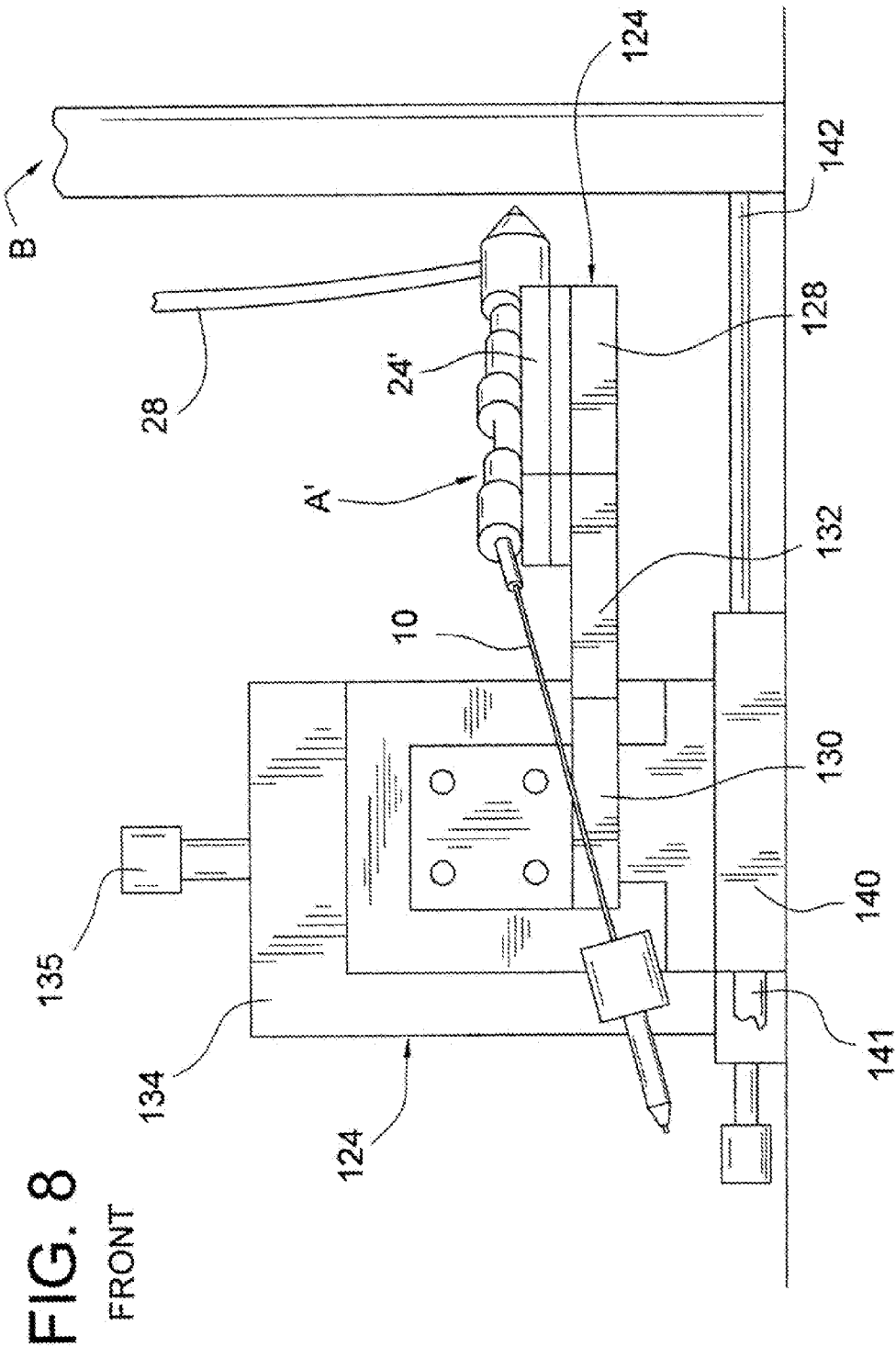

NANO-ELECTROSPRAY NEBULIZER

CROSS-REFERENCE TO RELATED APPLICATIONS

The subject matter of this application is disclosed in Provisional Application Ser. No. 60/560,462, filed Apr. 8, 2004 and priority is hereby claimed thereon.

STATEMENT REGARDING FEDERALLY SPONSORED RESEARCH OR DEVELOPMENT

Not Applicable

REFERENCE TO A "SEQUENCE LISTING", A TABLE, OR A COMPUTER PROGRAM LISTING APPENDIX SUBMITTED ON COMPACT DISC

Not Applicable

BACKGROUND OF THE INVENTION

1. Field of the Invention

The present invention relates to a nano-electrospray nebulizer for use as an ion source for a mass spectrometer. More particularly, it relates to a nebulizer that facilitates alignment with the mass spectrometer target, reduces sample and nebulizer gas leakage, and is easy to assemble and disassemble so as to permit quick electrospray needle replacement for elimination of clogs, operation over a wide range of sample flow rates, including extremely low sample flow rates without loss of accuracy, and performance of both static and dynamic analysis.

Various types of mass spectrometers are available in the market. These include quadrupole, magnetic sector, Fourier transform ion cyclotron resonance and other time-of flight devices as well as hybrid combinations of mass spectrometers, (BEQQ, Q-Tof, TOF-TOF, Ion Trap-Fourier Transform, etc.).

Those mass spectrometers operate by causing charged molecules (ions) of the sample to be analyzed as a function of their mass to charge ratio. The separated ions are detected electronically. The detected quasi-molecular ions are detected as an ion current which is directly correlated to the different elements or empirical formulas of the compounds that make up the sample. Accordingly, mass spectrometers of the type here under consideration require an ion source that includes a means of ionizing the molecules of the sample to be analyzed while in solution phase.

2. Description of Prior Art Including Information Disclosed Under 37 CFR 1.97 and 1.98

Electrospray and nanospray techniques are conventionally utilized for converting an initially neutral sample into an ionized species in the gas phase. Devices utilizing those techniques are therefore commonly used as sources of ions for mass spectrometers.

Those ion sources consist of a needle assembly, which includes a very thin, hollow, inner metal or glass tube. The inlet side of the inner tube is connected through a housing to receive the sample to be analyzed. A liquid chromatographic column or an infusion pump may be used to supply the sample to the housing. The sample to be analyzed is normally supplied to the housing as a liquid formed of a solid in solution.

The needle assembly also includes a hollow, metal outer tube having an inner diameter that is slightly larger than the outer diameter of the inner glass tube. The inner tube is received within the outer tube such that the outer tube surrounds, but is spaced a short distance from, the inner tube, defining a space around the inner tube through which a nebulizer gas is pumped.

The outlet side of the needle assembly terminates in a chamber within the mass spectrometer. The walls of the outer metal tube electronically charged relative to the source chamber. The liquid sample is converted by the needle assembly into an electrostatically charged aerosol spray that is discharged from the needle assembly outlet into the chamber. The solvent in the liquid sample is evaporated. The analyte and solvent ions in the aerosol spray are moved by a vacuum pump from the chamber through a target having a conical aperture and are then drawn into the analyzer.

In practice, the outlet side of the needle assembly must be very precisely aligned with the target in order to deliver sufficient amounts of sample to the analyzer for analysis. In many designs, the needle assembly provides an ion spray that is aimed in a direction orthogonal to the axis of the target aperture. Accurate alignment of nebulizers with that structure, such as the electrospray ionizer supplied by Micromass UK Limited of Floats Road, Wythenshawe, M23 9LZ, U.K. with its Q-TOF 2 hybrid quadrupole time-of-flight mass spectrometer, involves painstaking and time-consuming adjustments to achieve the required alignment.

Aside from the alignment problems, sample and nebulizer gas leaks from the needle assembly commonly occur in the Micromass ion source. This is due to the structure of the housing that functions to connect the needle assembly inlet with the sample source and the nebulizer gas source.

Clogs in the needle assembly tend to be a common occurrence in ion sources utilizing the tube within a tube structure because of the very small inner diameter of the inner glass tube. In order to avoid having to replace the entire tube when a clog occurs, requiring removal of the nebulizer housing from its platform and the subsequent time consuming realignment of the needle assembly with the target, a "quick fix" is sometimes attempted in the Micromass ionizer by cutting off the end of the clogged inner glass tube from the remainder of the needle assembly. Unfortunately, that procedure often does not work well because cutting off the clogged portion of the inner tube frequently results in an uneven or jagged edge (on a microscopic scale) that alters the direction of the spray.

On the other hand, aside from the alignment problems noted above, replacement of the clogged needle assembly is also disadvantageous because the glass inner tube is extremely thin and fragile. It is very difficult to handle and breaks easily. Further, the ends of the inner glass tube are very sharp and the tube must be very handled carefully to avoid injuring the personnel setting up the apparatus.

For all of those reasons, set up of the analysis equipment is labor intensive and very time consuming. We have found that it sometimes requires several hours to set up a single analysis with the Micromass equipment.

Some conventional nebulizers designed for use with mass spectrometers, including the one supplied by Micromass for the above mentioned analyzer, have what is known as a "zero dead volume" design that is suppose to eliminate any gap or space between the sample supply conduit and the inlet of the inner tube of the needle assembly. Under low flow conditions, such a gap is undesirable because a "dead volume" within the housing results in a substantial time delay between the time the sample is introduced into the housing and the time that the ions are formed.

The Micromass needle assembly housing incorporates a blind recessed fitting to interface the inlet end of inner glass tube to the zero dead volume union. However, this structure increases the difficulty of the alignment of the assembly parts.

It also greatly increases the risk that a leaky connection will go unnoticed. The nebulizer of the present invention utilizes a structure at this interface that minimizes the alignment and leakage problems.

Conventional nebulizers, including the one from Micromass, tend not to operate well at very low liquid sample flow rates. Clogs in the needle assembly often result from such low flow rates, requiring removal of the nebulizer housing from its platform, cutting off of the clogged portion of the inner tube, and time consuming reassembly and realignment of the apparatus.

The nebulizer of the present invention allows for rapid changing of the needle assembly to a larger diameter inner glass tube with reduced chance for clogging and hence can be used over a wider range of flow rates. Since the diameter of the inner tube is proportional to its capacity and maximum flow rate, quick changing of the tube permits our apparatus to accommodate flow rates from as low as 20 nanoliters/minute to as much as 200 microliters/minute, a dynamic range of 1000.

Further, we are able to interface our source to a variety of different supplies, from a 75 micron inner diameter liquid chromatographic (LC) column (having an optimum flow rate of 150 nanoliters/minute) to a 300 micron inner diameter LC column (having an optimum flow rate of 2 microliters/minute) and a 2 millimeter inner diameter LC column (having an optimum flow rate of 200 microliters/minute). This provides greatly enhanced versatility.

Another feature of our ionizer structure is that it can reproducibly be installed "off the shelf" in a much shorter time than the Micromass design because the parts are self-aligning and easier to assemble. In part, this is due to the use of a "snap-in snap-out" spring clip mechanism that is keyed to reproducibly align the needle assembly with the previous micrometer settings, along the X, Y and Z directions. The Micromass equipment has no comparable structure and can only be adjusted in two directions.

Our design also allows the flexibility of screwing it directly into a capillary column sample supply. This reduces the unwanted dead volume in the housing and hence the amount of time it takes to begin the analysis. For example, a 500 nanoliter dead volume will take ten minutes to fill at 50 nanoliters/minute.

The present invention has a mounting platform for the needle assembly housing that is aimed at a 45 degree angle relative to the axis of the target. That configuration allows for a greater cross-sectional area of the ion spray to enter the target aperture, as compared to the orthogonal approach utilized by Micromass.

Different nebulizers with different size needles are required for static and for dynamic analysis. The Micromass equipment requires time consuming reassembly and realignment when changing between types of analysis. That problem is largely eliminated with our design because of the ease by which the needle assembly can be replaced.

It is, therefore, a prime object of the present invention to provide a nano-electrospray nebulizer for use with a mass spectrometer that facilitates assembly and alignment of the needle assembly.

It is another object of the present invention to provide a nano-electrospray nebulizer that facilitates quick and easy removal and/or replacement of the inner tube of the needle assembly to eliminate clogs, and to permit use of the nebulizer with samples having a wide range of sample flow rates and for both static and dynamic analysis.

It is another object of the present invention to provide a nano-electrospray nebulizer structure that greatly reduces sample and nebulizer gas leaks.

It is another object of the present invention to provide a nano-electrospray nebulizer structure that reduces the dead volume within the needle assembly housing and hence speeds up the analysis.

It is another object of the present invention to provide a nano-electrospray nebulizer structure that is adjustable in three directions to facilitate target alignment.

It is another object of the present invention to provide a nano-electrospray nebulizer structure that includes a spring clip mechanism permitting the needle assembly housing to be quickly and easily removed from and mounted on the mounting platform without disturbing the previous alignment setting.

It is another object of the present invention to provide a nano-electrospray nebulizer which is capable of operating at extremely low liquid sample flow rates, thereby requiring less sample material, without loss of sensitivity or accuracy, or significant reduction in signal-to-noise ratio.

It is another object of the present invention to provide a nano-electrospray nebulizer structure in which the needle assembly housing mounting platform is oriented at a 45 degree angle relative to the target axis to increase the amount of ions entering the target.

BRIEF SUMMARY OF THE INVENTION

In accordance with one aspect of the present invention, a nebulizer is provided for use as an ion source for a mass spectrometer. The nebulizer is adapted to be used with a supply of sample and a nebulizer gas supply. The nebulizer includes a needle assembly. The needle assembly consists of an inner tube and an outer tube. The inner tube is received within the outer tube so as to define a nebulizer gas channel therebetween. A nozzle is provided. The nozzle has a channel with a portion adapted to retain the outer tube of the needle assembly. Means are provided for connecting the nebulizer gas supply to the nebulizer gas channel. Inner tube clamping means are connected to the nozzle. The clamping means has a channel aligned with the nozzle channel. A housing with a channel having first and second portions is provided. The first housing channel portion is adapted to receive the nozzle the inner tube clamping means. Means are provided for connecting the sample supply to the second portion of the housing channel. The inner tube extends through the outer tube, the nozzle channel, the inner tube clamping means channel and the second housing channel portion, with the inlet end situated to receive the sample.

The nozzle includes a rear section. The inner tube clamping means is received in the rear section of the nozzle.

The nozzle channel portion that retains the outer needle of the needle assembly has an inner diameter approximately equal to the outer diameter of the outer tube. It is situated in the forward section of the nozzle.

The nozzle channel has a second portion with an inner diameter substantially larger than the outer diameter of the inner tube. That portion of the nozzle channel is situated in the middle and rear sections of the nozzle.

The rear section of the nozzle has a substantially cylindrical shape. That section of the nozzle has an externally threaded surface. The inner tube clamping means is received in a recess in the rear section of the nozzle.

The housing channel has internally threaded surface adapted to engage the externally threaded surface of the rear section of the nozzle. It also has a surface that is inclined relative to the axis of the housing. The inner tube clamping means has a part with a surface inclined relative to the axis of the nozzle. That part is adapted to press against the inclined surface of the housing channel, as the nozzle is received within the housing channel.

The inner tube clamping means preferably takes the form of a ferrule. The ferrule includes a part adapted to be compressed to engage the inner tube. The inclined surface of the housing channel presses against the ferrule part to compress the ferrule to engage the inner tube as the nozzle is screwed into the housing.

A section of tubing formed of a compressible material, such as Poly Ether Ether Ketone (PEEK), is situated between the inner tube clamping means and the inner tube. When the ferrule part is compressed to engage the inner tube, the PEEK tubing creates a seal between the ferrule and the inner tube. It also protects the fragile inner tube.

The present invention also includes a mounting platform having a recess into which the housing is received. Spring clip means are provided to retain the housing in the platform recess. Preferably, the spring clip means comprises a spring clip that permits the housing to be removed from and received in the platform recess without altering the position of the platform relative to the target.

The nebulizer is designed for use with a mass spectrometer having a sample target with an axis. Means are provided for mounting the housing with the needle assembly situated at a 45 degree angle relative to the target axis. Means are also provided for mounting the housing for adjustment relative to the target axis in three directions.

In accordance with another aspect of the present invention, a nebulizer is provided for use as an ion source for a mass spectrometer, the nebulizer includes a needle assembly. The needle assembly includes an inner tube and an outer tube. The inner tube is received within the outer tube. A nozzle is provided. The nozzle retains the outer tube of the needle assembly. Compressible means are mounted on the nozzle. A housing is provided with a channel. The nozzle is moveably received within the housing channel. It is movable relative to the housing between a first position, wherein the compressible means is in the uncompressed state and does not engage the inner tube, and a second position, wherein the compressible means is compressed to engage the inner tube. The inner tube extends through the outer tube, the compressible means and into the housing channel.

The nozzle is rotatably received within the housing channel. The housing channel includes an interior surface with a substantially conical portion. The compressible means includes a part adapted to cooperate with the conical housing channel portion to compress the compressible means.

The compressible means includes first and second normally spaced parts adapted to cooperate with the conical housing channel portion. As the nozzle is screwed into the housing, the parts of the compressible means move towards each other to engage the inner tube. The compressible means preferably takes the form of a ferrule.

The nozzle has a rear section, to which the compressible means is connected. The rear section of the nozzle has a substantially cylindrical shape, and is externally threaded. The rear section of nozzle, which carries the compressible means, is received in the housing channel.

The housing channel has an interior surface with a substantially conical portion. The compressible means includes a part adapted to cooperate with the conical housing channel portion to compress the compressible means, as the nozzle is rotated relative to the housing.

The nozzle has a channel with a first portion having an inner diameter approximately equal to the outer diameter of the outer tube. That portion retains the outer tube.

The nozzle channel also has a second portion. That portion has an inner diameter substantially larger than the outer diameter of the inner tube.

Compressible tubing is situated between the compressible means and the inner tube. The compressible tubing extends into the second portion of the nozzle channel.

The rear section of the nozzle has a recess. A portion of the compressible means is received within the recess in the rear section of the nozzle.

The nebulizer further comprises a mounting platform. The platform has a recess into which the housing is received. Spring clip means are provided for retaining the housing in the mounting platform recess.

The nebulizer of the present invention is designed for use with a mass spectrometer having a sample target with an axis. It includes means for mounting the housing at a 45 degree angle relative to the target axis. Means are also provided for mounting the housing for adjustment relative to the target axis in three directions.

BRIEF DESCRIPTION OF THE SEVERAL VIEWS OF DRAWINGS

To those and to such other objects that may hereinafter appear, the present application relates to a nano-electrospray nebulizer, as described in detail in the following specification, and recited in the annexed claims, taken together with the accompanying drawings, wherein like numerals refer to like parts, and in which:

FIG. 4 is a side view of the ferrule that functions to clamp the inner tube;

FIG. 5 is a front view of the ferrule of FIG. 4;

FIG. 8 is a front view of the nebulizer and mounting platform.

Figure 1:
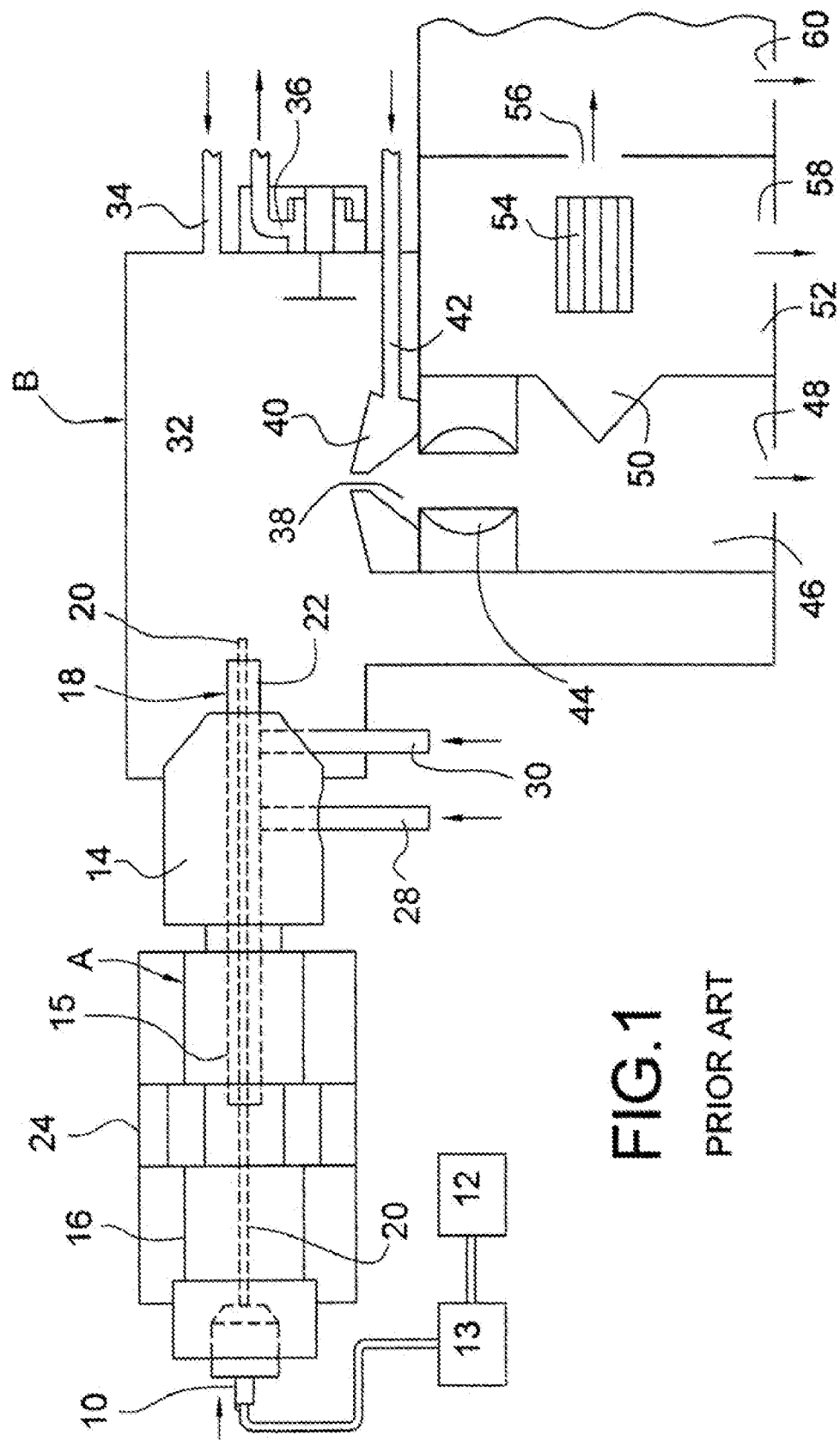
FIG. 1 is a schematic view of a prior art mass spectrometer with an ion source connected thereto.

FIG. 1 is an idealized drawing of a conventional ion source, generally designated A, designed for use with a conventional time of flight type mass spectrometer, generally designated B. The inlet end of nebulizer A is connected to one end of a sample supply conduit 10. The other end of conduit 10 is connected to a supply vessel 12 containing the sample to be analyzed, through an infusion pump 13. The sample in sample supply vessel 12 is preferably in liquid form, such as a solid in solution.

Nebulizer A includes a nozzle 14. Nozzle 14 is mounted on the front end of an elongated housing 16. A needle assembly 18 is situated in an axial channel 15 that extends through the nozzle and the housing. The inlet end of needle assembly 18 is connected through the housing to receive the sample.

The outlet end of needle assembly 18 extends a short distance beyond the conically shaped front surface of nozzle 14. Needle assembly 18 includes a very thin inner fused silica glass capillary tube 20. Inner tube 20 is received within a larger diameter metal outer tube 22. Inner tube 20 extends a short distance beyond outer tube 22 at its outlet end, right as seen in the drawing. It also extends a considerable distance beyond the rear end of outer tube 22, left as seen in the drawing, such that the inlet end of inner tube 20 receives the sample from conduit 10. The liquid sample travels from conduit 10, through needle assembly 18, where it is converted into a fine spray of ions that is ejected from the outlet end of the needle assembly, into mass spectrometer B.

Housing 16 is received in a recess in a mounting platform 24. Platform 24 is situated adjacent to the mass spectrometer B such that the nebulizer provides a spray of ions to the mass spectrometer for analysis.

Nozzle 14 includes a radially directed nebulizer gas channel 26 adapted to receive one end of a nebulizer gas supply conduit 28. The other end of conduit 28 is connected to a supply of nebulizer gas (not shown.) Nitrogen is often used as the nebulizer gas. Conduit 28 is connected to provide the nebulizer gas to the space between the exterior surface of inner tube 20 and the interior surface of outer tube 22.

A desolvation gas supply conduit 30 is connected through nozzle 14 to the space in channel 15 surrounding the exterior surface of outer tube 22. The other end of conduit 30 is connected to a supply of desolvation gas (not shown.)

The outlet end of the needle assembly 18 to situated proximate an enclosure 32 within mass spectrometer B. The walls of enclosure 32 are maintained at an electric potential relative to the conductive outer tube of the needle assembly such that the molecules of the liquid sample are in an ionized state when they move through the mass spectrometer.

A magnetic field is applied across enclosure 32 such that the ions leaving the needle assembly separate in accordance with their mass/charge ratio as they traverse the chamber. Purge gas can be introduced into and removed from enclosure 32 through ports 34 and 36, respectively. A cleanable baffle 38 is situated adjacent the purge gas ports.

Some of the ions from the nebulizer enter the mouth of a cone 40 with an aperture, which is the sample target. Cone 40 is connected by conduit 42 to a supply of cone gas (not shown.) In this design, the needle assembly 18 is situated at a right angle relative to the axis of the target cone.

The ions move through the aperture in cone 40, passed an isolation valve 44 to a second chamber 46. A port 48 in chamber 46 is connected to a rotary pump (not shown) that causes the ions to move through an extraction cone 50 into a chamber 52.

An RF lens 54 situated in chamber 52 is used to focus the ions passing through the extraction cone 50 into an aperture 54. Turbomolecular pumps (not shown) connected to ports 58, 60 may be utilized to assist the movement of the ions through the lens 54, aperture 56 and into the analyzer.

The nebulizer A' of the present invention is illustrated in FIGS. 2-8. As seen in detail in FIGS. 2, 3 and 6, nebulizer A' includes a nozzle 14' and a housing 16'. As in the nebulizer of FIG. 1, nozzle 14' is mounted on housing 16' which is received within the recess of a mounting platform 24'.

Housing 16' has a generally cylindrical configuration. It has a polygon shaped mid-section 62 between the forward and rear cylindrical sections 64, 66. Housing sections 62, 64 and 66 are received in correspondingly shaped portions of the recess in the mounting platform 24'.

Nozzle 14' includes a conical forward section 68, a generally cylindrical middle section 70 and a generally cylindrical, externally threaded, rear section 72. The forward section has a port 74 for connection to a conduit for supplying nebulizer gas to the nozzle.

The rear section 72 of nozzle 14' has a smaller diameter than middle section 70. The exterior surface of section 72 is externally threaded. Rear section 72 of nozzle 14' is designed to be rotatably received in the front end of housing 16' and to extend beyond the front of platform 24'.

The externally threaded rear section 72 of the nozzle is adapted to be rotatably received within the internally threaded front portion 76a of a channel 76 that extends axially through housing 16'. A ferrule 78 is mounted in rear section 72 of nozzle 14'. Ferrule 78 has a conically shaped rear surface 80 divided into normally spaced parts 82, 84, see FIGS. 4 and 5.

The needle assembly 18' consists of a very thin, hollow inner capillary tube 20', preferably made of fused silica glass, and a hollow, outer tube 22', made of electrically conductive material, such as stainless steel. The forward portion of inner tube 20' is received within outer tube 22'. The inner diameter of outer tube 22', for example, 0.016 in., is larger than the outer diameter of inner tube 20', for example 0.014 in., by a very small distance, forming a nebulizer gas channel 86 therebetween. Port 74 is connected to the nebulizer gas channel through the middle section of a channel 88 that extends axially through nozzle 14'.

Figure 3:
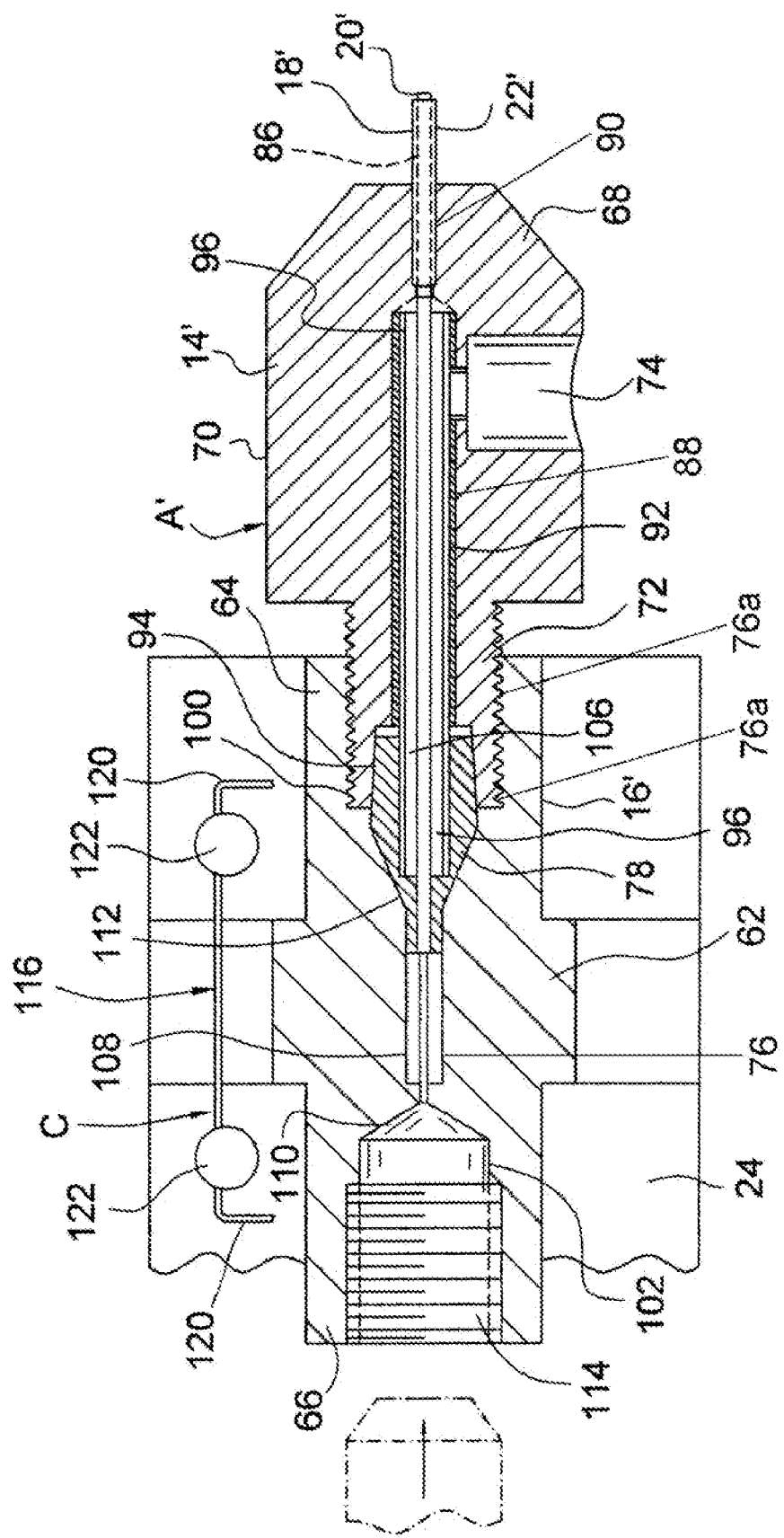
FIG. 3 is a cross-sectional view of the nebulizer of the present invention.
Figure 6:
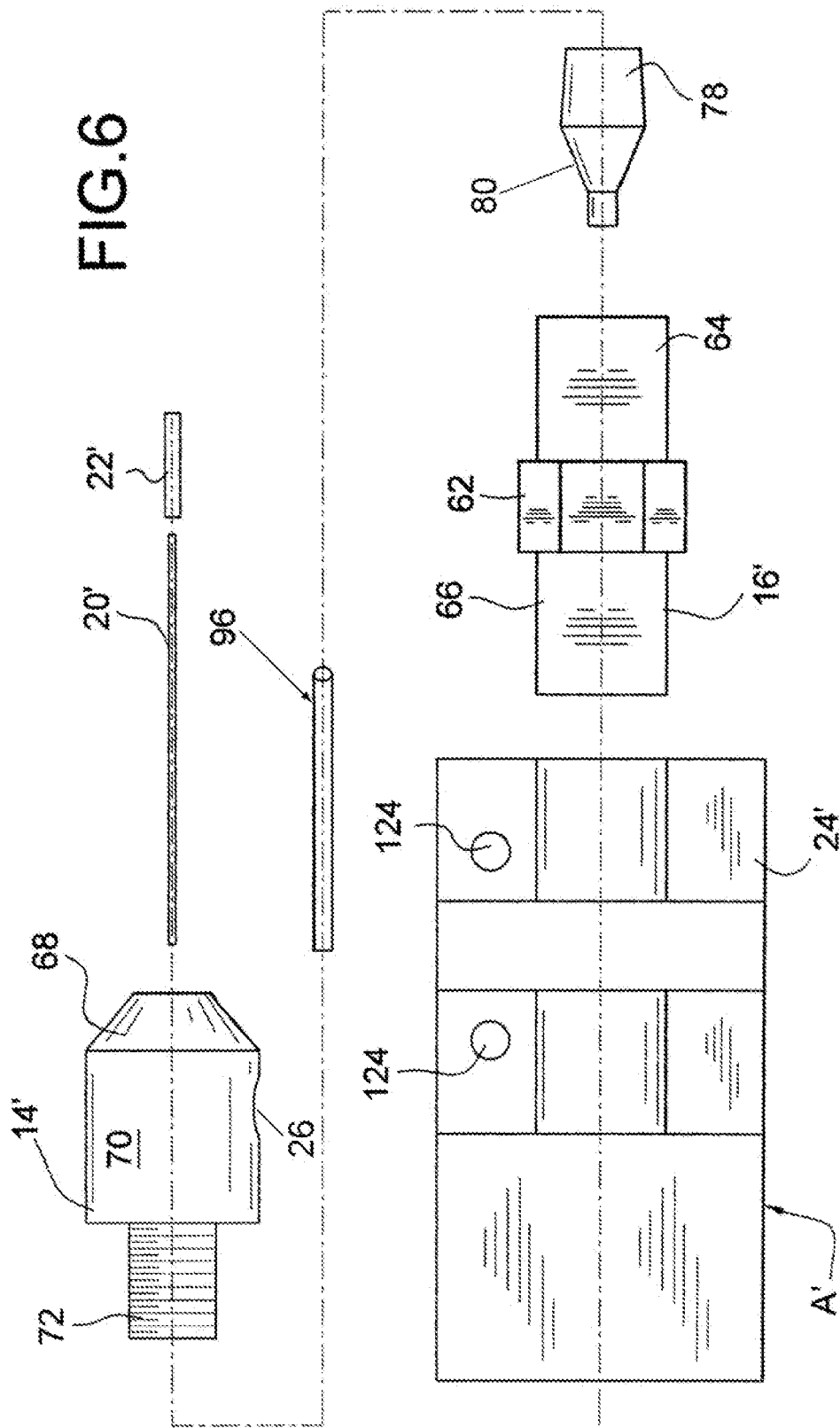
FIG. 6 is an exploded view of the nebulizer of the present invention.

Nozzle channel 88 has three sections. The forward section 90 of the channel extends through the forward section of nozzle 14' and has an inner diameter substantially equal to the outer diameter of outer tube 22' so at to fixedly retain the outer tube 22'. The middle channel section 92 has a substantially larger diameter, as compared to that of section 90, and is connected to port 74 to receive the nebulizer gas. The rear section 94 of the nozzle channel has an even larger diameter, defined by a slightly tapered interior surface, and is adapted to fixedly receive ferrule 78 therein. As seen in FIG. 3, inner tube 20' extends through the outer tube 22' in forward channel portion 90, the middle channel portion 92 and through the ferrule lodged within the rear channel portion 94.

A tubular lining 96 formed of compressible material such as Poly Ether Ether Ketone (PEEK) is received around the portion of inner tube 20' within ferrule 78 and forwardly into middle nozzle channel section 92. The purpose of lining 96 is to uniformly distribute the pressure from the ferrule radially inwards towards the fragile inner tube 20' when the inner tube is engaged by the split parts 82, 84 of the rear end of ferrule 78, as described in detail below. The PEEK material is chosen because it is generally chemically inert and therefore will not dissolve in the liquid chromatograph solvents.

When the inner tube 20' is slipped through the PEEK lining tube 96 and the rear, externally threaded section 72 of nozzle 14' is rotatably received within the internally threaded forward section 98 of channel 100 in housing 16', the compression fitting formed by the compression of the rear portion of ferrule 78 allows for seamless transfer of eluent from the sample supply, such as a liquid chromatographic column or syringe, directly to the mass spectrometer. In this case, the rear section 102 of housing channel 100 may be internally threaded to receive a connector 102 that is, in turn, directly connected to the sample supply, which may be an LC column, a syringe or any other type of vessel.

The forward portion 104 of tubing 96 extends through an enlarged channel 106 within ferrule 78 and into nozzle channel section 92. That portion of tubing 96 is not compressed by the ferrule parts as they are moved towards each other to engage the inner tube. This allows the nebulizer gas, which may be compressed nitrogen, supplied to the nozzle through port 74, to flow freely around the tubing 96. The nebulizer gas flows coaxially between the outside surface of the inner tube and the inside surface of the outer tube, towards the outlet end of the needle assembly.

Axial channel 106 of ferrule 78 aligns with, and is approximately the same diameter as, channel portion 92 in nozzle 14'. Lining tube 96 extends from a point just forward of parts 82, 84 that form the rear portion of ferrule 78 forward through housing channel portion 92. Inner tube 20' extends rearwardly from outer tube 22', which is retained in forward portion of the nozzle channel, through housing channel portion 92, ferrule 78 and through the middle section 108 the housing channel to the rear section 102 of the housing channel. The inlet end of inner tube 20' is situated at the center of the conical front surface 110 of housing channel section 102 so as to receive the sample directly from connector 104 received within section 102

Ferrule 78 engages the inner needle assembly tube 20' at the point where the inner tube exits the ferrule and enters housing channel portion 108. As best seen in FIGS. 4 and 5, the conical split rear portion of ferrule 78, consisting of parts 82 and 84, is situated to press against a correspondingly shaped conical surface portion 112 of housing channel 74 when the ferrule is received in the housing channel. The inclination of the exterior surfaces of each of the parts 82, 84 substantially corresponds to the inclination of conical surface portion 112 of the housing channel. When the ferrule is pressed against that portion of the housing channel, parts 82 and 84 are moved toward each other (compressed) to compress tubular lining 96 and securely engage the inner tube 20'.

As the rear section 72 of nozzle 14' is rotatably received within the forward section 98 of the housing channel, the external threads of surface 72 engaging the internal threads of channel section 98, ferrule 78 is moves axially toward the inlet end of housing 16'. That causes the rear section of the ferrule to bear against the conical portion 112 of the housing channel, which in turn causes parts 82 and 84 to move together to compress tubular lining 96 and engage the inner tube, at a point a short distance from the inlet end of the inner tube.

Rotating nozzle 14' relative to housing 16' in the opposite direction will cause the nozzle to move axially away from the inlet end of the housing, permitting ferrule parts 82, 84 to move apart, releasing the inner assembly tube. Once released from ferrule 78, the inner tube can be removed from the nozzle, for example, in the event of a clog. A new inner tube can then be inserted into the nozzle. The nozzle is then rotated relative to the housing to cause the ferrule to clamp the new inner tube in place. Since the position of the mounting platform remains undisturbed during the inner tube replacement procedure, no time consuming realignment is required.

By way of contrast, when the inner glass tube clogs in the Micromass ion source, if the entire inner tube is removed, the assembly must be completely realigned before the analysis can continue. If the "quick fix" is attempted, where the forward portion of the inner tube is cut off without realigning the entire assembly, the cut often results in an uneven or jagged edge (on a microscopic scale) and the direction of the spray will be changed. Our invention avoids this problem by permitting a fresh inner needle assembly needle to be installed into the nebulizer quickly and easily, without the need for realignment.

The internal threads 114 of nozzle channel portion 102 permit the nebulizer to be screwed directly into a capillary column, reducing unwanted dead volume in the source. This is important because a dead volume even as small as 500 nanoliters will take 10 minutes to fill at 50 nanoliters/min.

As mentioned previously, the nebulizer of the present invention can be used with very low sample flow rates without loss of sensitivity. When the flow of analyte through inner tube is high, for example 200 nanoliters per minute, a relatively high nebulizer gas pressure is used to "blow" the liquid sample stream off the output end of the inner needle assembly tube in order to form an aerosol comprised of electrically charged ions.

On the other hand, if the flow of analyte is quite low, for example 20-50 nanoliters per minute, there will be a tendency for the liquid analyte to wick on the tip of the inner needle assembly tube. If the surface tension of the liquid is high enough, a stable spray may not be achieved if the droplet meanders backwards down the nebulizer gas channel between the inner tube and the outer tube because of capillary action. In order to compensate for this, the pressure of the nebulizer gas can be adjusted so that the droplet remains intact, thereby permitting the nebulizer of the present invention to be used with very low sample flow rates.

Figure 2:
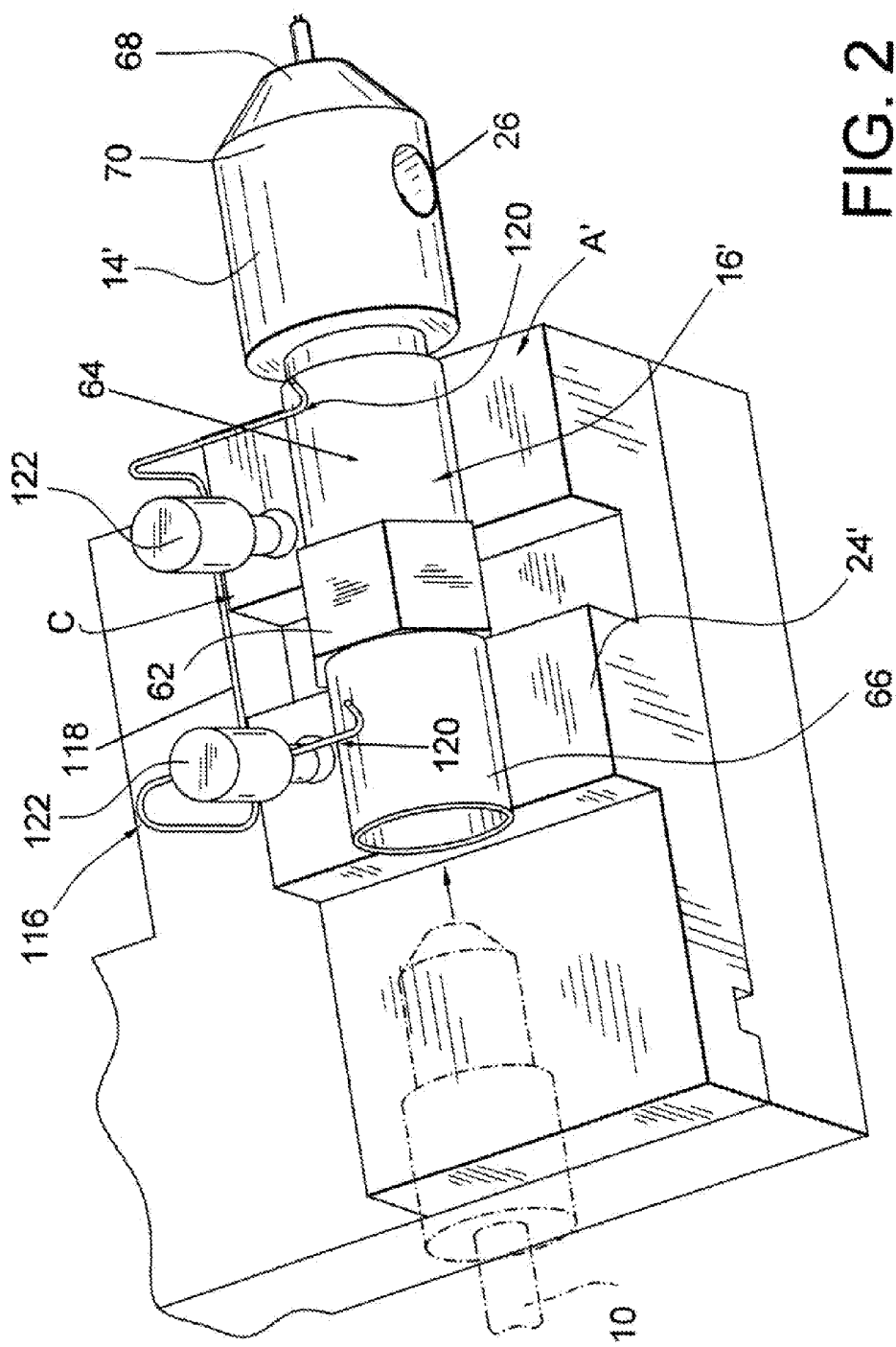
FIG. 2 is an isometric view of the nebulizer of the present invention situated on its mounting platform.

As best seen in FIGS. 2 and 3, a spring clip, generally designated C, is employed to retain housing 16' in position on mounting platform 24' and permit easy removal and replacement of the nebulizer. Spring clip C consists of a single, generally "u" shaped wire spring 116. Spring 116 consists of a section 118 that extends in a direction substantially parallel to the axis of housing 16' and parallel side sections 120 respectively extending from the opposite ends of section 118 towards and over the housing. Section 118 of the spring extends through aligned openings in spaced screws 122. Screws 122 are rotatably received in openings 124 on the surface of platform 24'.

Spring clip C is rotatable about section 118 between a closed position, illustrated in FIG. 2, wherein the ends of side sections 120 are situated adjacent to and press against the top of the housing, and an open position, approximately 90 degrees from the closed position, when side sections 120 are remote from the housing. In the closed position, the ends of side sections 120 bear down on the housing to retain the housing securely in a fixed position relative to the mounting platform. When the spring clip is moved to its open position, the housing can be easily removed from the platform. The shape of the spring clip urges it toward its open and closed positions such that a small amount of force must be applied to move the spring clip between positions.

Figure 7:
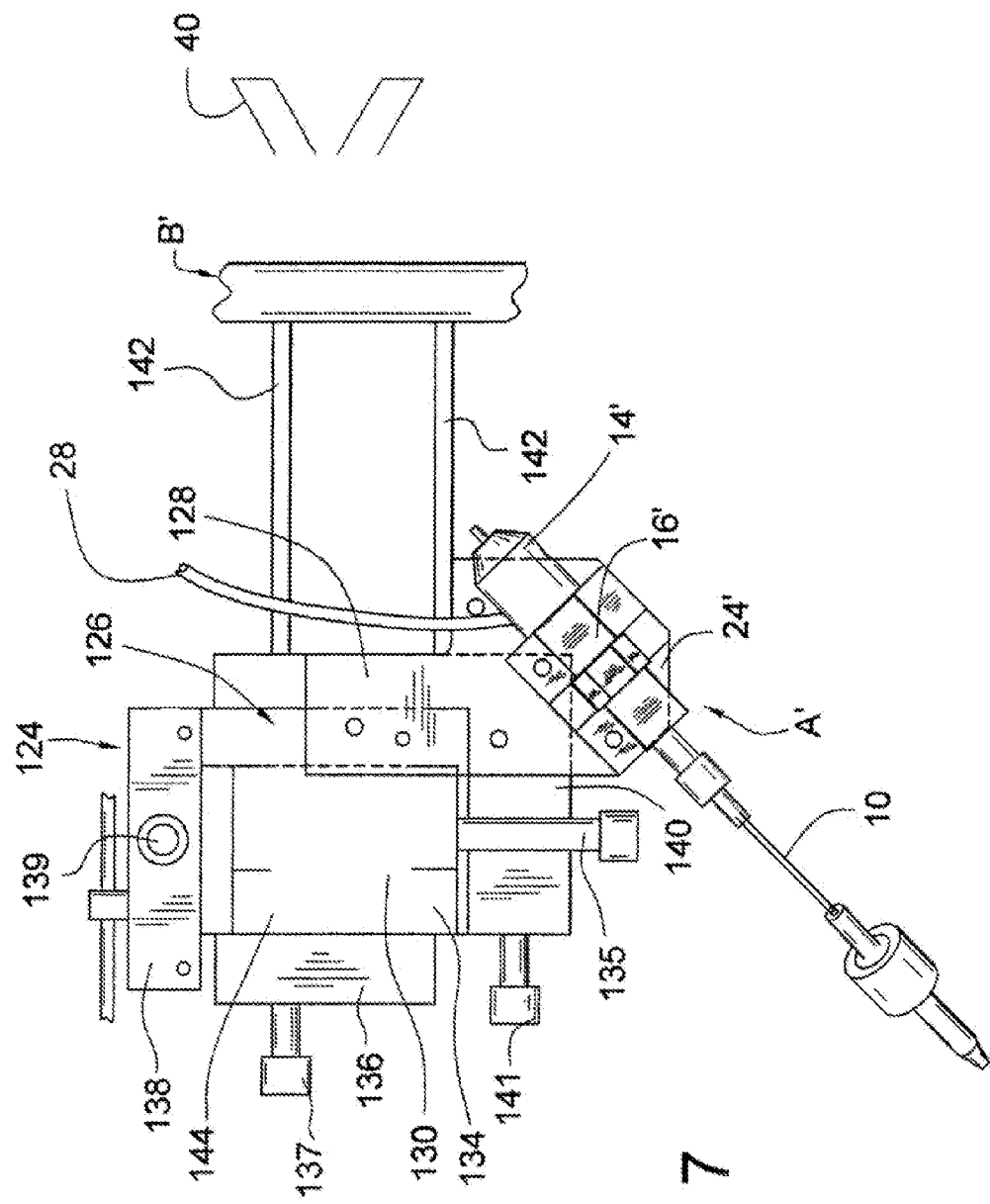
FIG. 7 is a top elevation view of the nebulizer mounted on its mounting platform.

Mounting platform 24' is situated on a position adjustment means 124 and is supported on a support 126 that is connected to means 124, as seen in FIGS. 7 and 8. Referring to FIG. 7, which is a top view of the assembly, support 126 includes a forward portion 128, upon which platform 24' is situated, and a rear portion 130 that is attached to a position adjustment means 124. Portion 128 and portion 130 are connected by an intermediate portion 132. Support 126 is preferably made of insulating material, such as plastic.

From FIG. 7 it will be readily appreciated that the shape of support 126 is such that the platform 24', and thus the needle assembly of the nebulizer of the present invention, is situated at a 45 degree angle relative to the axis of target 40. That design permits more of the ionized spray to enter the target, as compared to the conventional orthogonal approach.

Position adjustment means 124 permits support 126, and hence the nebulizer, to be independently aligned with the target in three orthogonal directions, X, Y and Z. Means 124 consists of three independently moveable blocks 134, 136 and 138. Each block includes a rotatable control knob 135, 137, 139 respectively that carries an internal gear (not shown.) The gear engages an internal rack (also not shown) such that rotation of the knob causes the block to move back and forth in a single direction relative to the rack. Each control knob is calibrated much like a micrometer so that it can be accurately set. By combining these blocks together as illustrated, the position of support 126 relative to the target can be independently adjusted in three directions.

Means 124 is mounted upon a base 140. Base 140 is situated on a pair of parallel rods 142 extending from the wall of mass spectrometer B. A control knob 141 is associated with base 140. Rotating knob 141 releases rods 142 such that base 140 can be moved along rods 142 to space the base from the mass spectrometer wall. Rotating knob 141 sets the base in that position.

Block 134 is mounted on the upper surface of base 142. Rotating knob 143 causes block 134 to move relative to base 140 in a direction (X) toward and away from the mass spectrometer wall. Block 136 is mounted on top of block 134. Rotating know 137 causes block 136 to move relative to block 134 in a direction (Y) parallel to the mass spectrometer wall. Block 138 is mounted on block 136. Rotating know 139 causes block 138 to move in a direction (Z) up and down relative to the wall. Support 126 is mounted to block 138 by an angle bracket 144. Manipulating the three control knobs accurately positions the nebulizer relative to the target in three directions.

It should now be appreciated that the present invention related to a nano-electrospray nebulizer for use as an ion source for a mass spectrometer in which the assembly and alignment problems commonly associated with ion sources of this type are greatly reduced by forming the apparatus from simple, interlocking and self-aligning parts which permit quick and easy removal and replacement of the inner tube of the needle assembly. Sample and nebulizer gas leakage from the apparatus is minimized. The gap between the sample supply conduit and the inlet end of the inner tube of the needle assembly is eliminated such that there is not dead volume present in the housing to slow down the analysis. The nebulizer functions well under very low sample flow rate conditions and is suitable for use in both static and dynamic analysis.

While only a single preferred embodiment of the present invention has been disclosed for purposes of illustration, it is obvious that many variations and modifications could be made thereto. It is intended to cover all of those variations and modifications, which fall within the scope of the present invention, as, defined by the following claims:

We claim:

1. A nebulizer for use as an ion source for a mass spectrometer, adapted for use with a sample supply and a nebulizer gas supply, said nebulizer comprising: a needle assembly, said needle assembly comprising an inner tube and an outer tube, said inner tube having an inlet end and a portion received within said outer tube, so as to define a nebulizer gas channel therebetween; a nozzle, said nozzle comprising a channel with a portion adapted to retain said outer tube; means for connecting said nebulizer gas supply to said nebulizer gas channel; inner tube clamping means, said inner tube clamping means being connected to said nozzle and having a channel aligned with said nozzle channel; a housing, said housing comprising a channel having first and second portions, said first housing channel portion being adapted to receive said inner tube clamping means; means for connecting said sample supply to said second portion of said housing channel, said inner tube extending through said outer tube, said nozzle channel, said inner tube clamping means channel and said housing channel, with said inlet end situated in said second housing channel portion to receive the sample.

2. The nebulizer of claim 1 wherein said nozzle comprises a rear section, and wherein said inner tube clamping means is received in said rear section of said nozzle.

3. The nebulizer of claim 1 wherein said outer tube retaining portion of said nozzle channel has an inner diameter substantially equal to the outer diameter of said outer tube.

4. The nebulizer of claim 1 wherein said nozzle comprises a forward section and said outer tube retaining portion of said nozzle channel is situated in said forward section of said nozzle.

5. The nebulizer of claim 1 wherein said nozzle channel comprises a second portion having an inner diameter substantially larger than the outer diameter of said inner tube.

6. The nebulizer of claim 1 wherein said nozzle has a middle section and wherein said second nozzle channel portion is situated in said middle section of said nozzle.

7. The nebulizer of claim 6 wherein said nozzle has a rear section and wherein said second nozzle channel portion is situated in said middle section and said rear section of said nozzle.

8. The nebulizer of claim 2 wherein said rear section of said nozzle has a substantially cylindrical shape.

9. The nebulizer of claim 2 wherein said rear section of said nozzle has an externally threaded surface.

10. The nebulizer of claim 2 wherein said rear section of said nozzle comprises a recess into which a portion of said inner tube clamping means is received.

11. The nebulizer of claim 1 wherein said housing has an axis and wherein a portion of the surface of said housing channel is inclined relative to said axis of said housing.

12. The nebulizer of claim 11 wherein said nozzle has an axis and wherein said inner tube clamping means comprises a part with a surface inclined relative to said axis of said nozzle, said inclined surface of said inner tube clamping means part being adapted to press against said inclined surface of said housing channel as said nozzle is received within said housing channel.

13. The nebulizer of claim 1 wherein said inner tube clamping means comprises a ferrule.

14. The nebulizer of claim 12 wherein said inner tube clamping means comprises a ferrule.

15. The nebulizer of claim 12 wherein said part of said inner tube clamping means is adapted to be compressed by said inclined surface of said housing channel to engage said inner tube.

16. The nebulizer of claim 1 further comprising compressible tubing situated between said inner tube clamping means and said inner tube.

17. The nebulizer of claim 1 further comprising a mounting platform having a recess into which said housing is received.

18. The nebulizer of claim 17 further comprising spring clip means for retaining said housing in said mounting platform recess.

19. The nebulizer of claim 1 for use with a mass spectrometer having a sample target with an axis, further comprising means for mounting said housing with said needle assembly situated at a 45 degree angle relative to said target axis.

20. The nebulizer of claim 1 for use with a mass spectrometer having a sample target with an axis, further comprising means for mounting said housing for adjustment relative to said target axis in three directions.

21. A nebulizer for use as an ion source for a mass spectrometer, the nebulizer comprising: a needle assembly, said needle assembly comprising an inner tube and an outer tube, said inner tube being received within said outer tube; a nozzle, said nozzle retaining said outer tube of said needle assembly; compressible means mounted on said nozzle; a housing with a channel, said nozzle being moveably received within said housing channel and movable relative therein between a first position, wherein said compressible means is in the uncompressed state and does not engage said inner tube, and a second position, wherein said compressible means is compressed to engage said inner tube, said inner tube extending through said outer tube, said compressible means and into said housing channel.

22. The nebulizer of claim 21 wherein said nozzle is rotatably received to said housing channel.

23. The nebulizer of claim 21 wherein said housing channel comprises an interior surface with a substantially conical portion.

24. The nebulizer of claim 23 wherein said compressible means comprises a part adapted to cooperate with said conical housing channel portion to compress said compressible means.

25. The nebulizer of claim 23 wherein said compressible means comprises first and second normally spaced parts adapted to cooperate with said conical housing channel portion to move towards each other to engage said inner tube.

26. The nebulizer of claim 21 wherein said compressible means comprises a ferrule.

27. The nebulizer of claim 21 wherein said nozzle comprises a rear section, and wherein said compressible means is connected to said rear section of said nozzle.

28. The nebulizer of claim 21 wherein said nozzle comprises a channel with a first portion having an inner diameter approximately equal to the outer diameter of said outer tube.

29. The nebulizer of claim 28 wherein said nozzle channel comprises a second portion having an inner diameter substantially larger than the outer diameter of said inner tube.

30. The nebulizer of claim 21 wherein a portion of said nozzle received in said housing channel has a substantially cylindrical shape.

31. The nebulizer of claim 30 wherein said portion of said nozzle has an externally threaded surface.

32. The nebulizer of claim 21 wherein said nozzle comprises a recess into which a portion of said compressible means is received.

33. The nebulizer of claim 21 further comprising compressible tubing situated between said compressible means and said inner tube.

34. The nebulizer of claim 21 further comprising a mounting platform having a recess into which said housing is received.

35. The nebulizer of claim 34 further comprising spring clip means for retaining said housing in said mounting platform recess.

36. The nebulizer of claim 21 for use with a mass spectrometer having a sample target with an axis, further comprising means for mounting said housing with said needle assembly situated at a 45 degree angle relative to said target axis.

37. The nebulizer of claim 21 for use with a mass spectrometer having a sample target with an axis, further comprising means for mounting said housing for adjustment relative to said target axis in three directions.

38. The nebulizer of claim 21 for use with a sample supply, wherein said inner tube has an inlet end situated within a portion of said housing channel and means for connecting the sample supply to said portion of said housing channel.

\* \* \* \* \*